United States Patent [19]

Brenholdt

[11] Patent Number: 4,543,482

[45] Date of Patent: Sep. 24, 1985

[54] TRANSDUCER MOUNTING ASSEMBLY

[75] Inventor: Irving R. Brenholdt, Stratford, Conn.

[73] Assignee: St. Regis Paper Company, West Nyack, N.Y.

[21] Appl. No.: 463,035

[22] Filed: Feb. 1, 1983

[51] Int. Cl.[4] ............................................. G01J 1/00
[52] U.S. Cl. .................................. 250/343; 250/359.1
[58] Field of Search ..................... 250/343, 349, 358.1, 250/359.1; 378/59

[56] References Cited

U.S. PATENT DOCUMENTS

| | | |
|---|---|---|
| 1,893,701 | 1/1933 | Glenn . |
| 2,759,175 | 8/1956 | Spalding . |
| 2,967,938 | 1/1961 | McKay et al. . |
| 3,445,655 | 5/1969 | Curry . |
| 3,519,824 | 7/1970 | Weinstock et al. . |
| 3,664,621 | 5/1972 | Savoie, Jr. . |
| 3,666,944 | 5/1972 | Baldinger .............................. 378/59 |
| 3,673,407 | 6/1972 | Wiswell, Jr. . |
| 3,952,204 | 4/1976 | Davis et al. ........................... 378/59 |
| 4,022,245 | 5/1977 | Davis . |
| 4,040,743 | 8/1977 | Villaume et al. . |
| 4,175,233 | 11/1979 | De Palma et al. ................... 250/343 |

Primary Examiner—Janice A. Howell
Attorney, Agent, or Firm—Kramer and Brufsky

[57] ABSTRACT

A transducer mounting assembly is provided for use in conjunction with apparatus for measuring the percentage of solid particles in a suspension flowing through a pipe. A hinged collar is adapted to be secured around a section of pipe. A radiant energy source is mounted at a first position on the circumference of the collar for radiating diffused radiant energy into the pipe. A first radiant energy detector is mounted at a second position on the circumference of the collar for sensing diffused energy in the pipe which is forward-scattered when a suspension flows therethrough. A second radiant energy detector is mounted at a third position on the circumference of the collar adjacent the first position for sensing diffused energy in the pipe which is back-scattered by a suspension flowing therethrough. A connector is provided for connecting the radiant energy source and detectors to a measuring apparatus.

19 Claims, 5 Drawing Figures

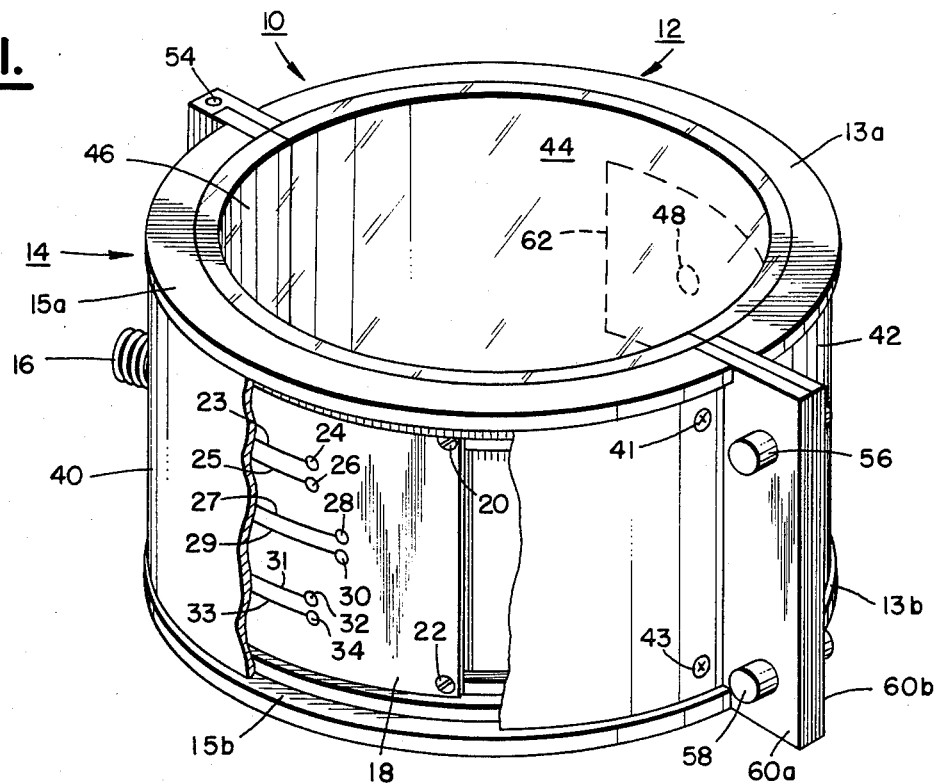
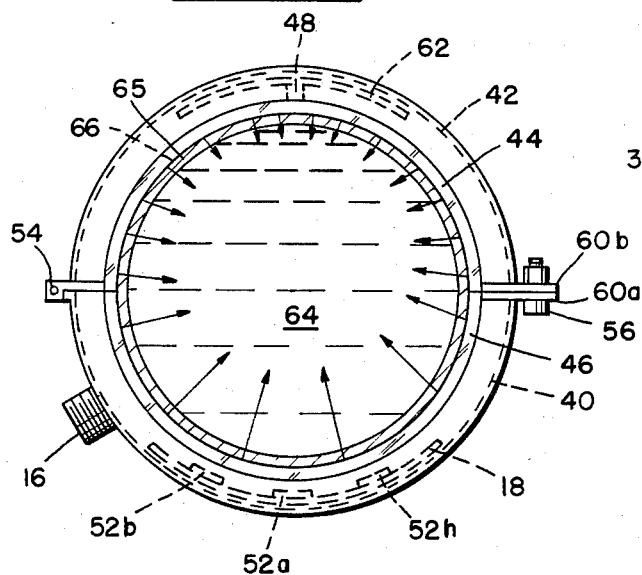
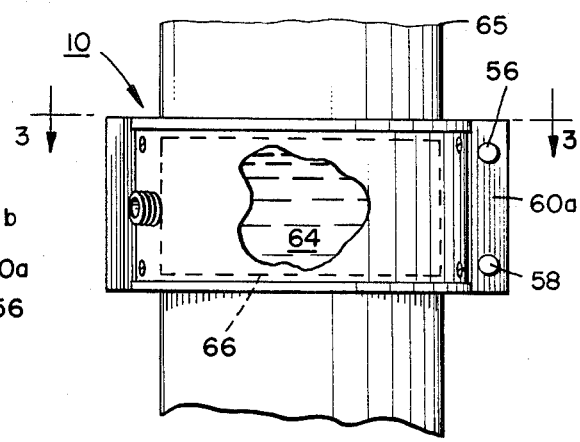
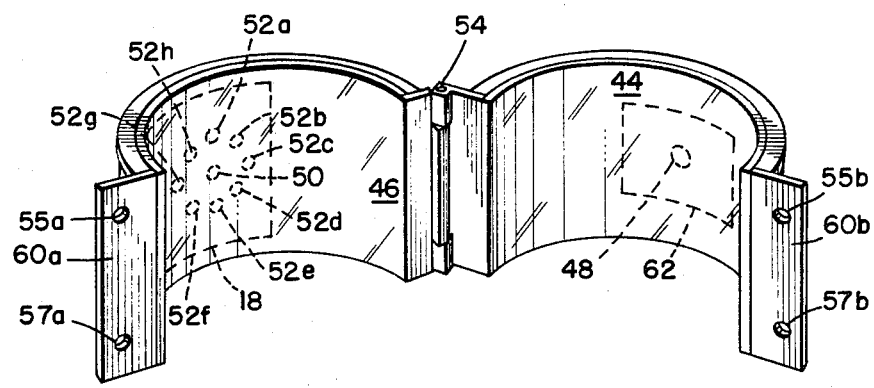

TRANSDUCER MOUNTING ASSEMBLY

BACKGROUND OF THE INVENTION

The present invention relates to a transducer mounting assembly for use in conjunction with an apparatus for determining the percentage of solid particles in a suspension ("consistency") and in particular to a transducer mounting assembly having a hinged collar adapted to be secured around a section of pipe having a suspension such as paper pulp stock flowing therethrough.

In paper manufacturing processes, the consistency of the pulp stock is a prime factor. For purposes of this disclosure the term "stock" is intended to mean wet pulp of any type at any stage in the paper manufacturing process. Different grades and weights of paper or paper products require different consistencies of stock. In addition, the consistency of pulp for a given paper product will depend on the process point at which a pulp sample is taken. The stock consists of the comminuted wood fibers, water, and sometimes certain additives. Such pulp stock is not a homogeneous mass, but rather is a mixture which contains the foregoing materials.

Since the consistency of the stock is of prime importance in the manufacturing of paper and paper products, it is highly desirable to know its consistency at all times. Further, in order to provide a reliable and high quality paper manufacturing operation, the consistency of unknown stock must be easily ascertained. Such a determination of consistency is particularly important when it is desired to switch a paper manufacturing apparatus from one grade of product to another. Such a grade change may necessitate the employment of stock having a different consistency.

The term "consistency" as used by the paper industry designates the concentration of pulp in water on a moisture-free basis. Consistency is expressed in terms of a percentage, with the percent consistency being calculated as follows:

$$\frac{\text{Moisture-free weight of pulp}}{\text{Weight of water and pulp}} \times 100 = \text{consistency (\%)}$$

In the pulp and paper industry, the consistency of stock may vary by three orders of magnitude, for example from 0.02% to 20%.

An apparatus and method for determining pulp stock consistency are disclosed in my co-pending U.S. Pat. No. 4,507,556 filed Dec. 8, 1982, which is incorporated herein by reference. A source of diffused radiant energy is provided which energy is directed toward a suspension to be measured. The portion of the energy which is forward-scattered by the suspension is detected and a first signal indicative of the magnitude of the forward-scattered energy is produced. The portion of energy which is back-scattered by the suspension is detected and a second signal indicative of the magnitude of back-scattered energy is produced. The first and second signals are combined at a predetermined ratio to produce a feedback signal used to control the intensity of energy emitted from the radiant energy source. The intensity of energy emitted from the source is a function of the forward-scattered and back-scattered energy and is directly proportional to the consistency of the suspension being measured. By monitoring the power driving the radiant energy source, a display calibrated in terms of percent consistency can be provided.

It is desirable to have a means for determining pulp stock consistency on a real-time basis during paper manufacture. facture. In order to accomplish this objective, means must be provided for monitoring the pulp stock as it flows through a process pipe. One way to accomplish this is disclosed in U.S. Pat. No. 4,040,743, wherein back-scattered, reflected, and transmitted energy is utilized to measure pulp slurry parameters. In this patent, an optical probe is provided within a molded housing which secures optics, windows and prisms in place and contains shoulders and an arcuate surface. The shoulders engage the outer surface of a pipe wall with a gasket disposed therebetween. An extension of the molded housing frictionally engages the walls of an aperture formed in the pipe wall. The probe assembly is secured in place by a strap. The arcuate surface of the molded housing and the windows lie in the plane described by the inner surface of the pipe wall. In order to use this structure, the pipe through which pulp stock is flowing must be cut open to provide the required aperture into which the molded probe housing fits. This results in a possibility of leakage and contamination of the pulp stock.

Various other patents disclose means for mounting radiation emitters and/or detectors around pipes or other cylindrical objects. For example, U.S. Pat. No. 2,759,175 relates to a leak detector for a pipe joint which uses a clamping arrangement for a thin, electrically conductive metal foil which surrounds the pipe joint. U.S. Pat. Nos. 2,967,938; 3,673,407; 3,519,824; and 3,445,655 all relate to various inspection means using some type of radiation emitter and detector in conjunction with a clamp for positioning the emitter and detector around a cylinder.

U.S. Pat. No. 4,022,245 discloses the use of a transparent sleeve around a check valve for visual inspection of the valve. The transparent window is not, however, used in conjunction with a radiation emitter and sensor arrangement which monitors parameters of a material flowing through a pipe.

clamping arrangements are shown in U.S. Pat. Nos. 1,893,702 and 3,664,621. Such arrangements do not relate to the mounting of radiation sources and detectors around a pipe for in-process measurement of desired parameters.

It would be advantageous to provide a transducer mounting assembly for use in conjunction with an apparatus for measuring the percentage of solid particles in a suspension flowing through a pipe. Such an assembly should provide for simple mounting to a pipe and subsequent removal from the pipe, and should not require any projection into an opening in the pipe which could result in leakage of a fluid from the pipe. The present invention relates to such a transducer mounting assembly.

SUMMARY OF THE INVENTION

A transducer mounting assembly for use in conjunction with apparatus for measuring the percentage of solid particles in a suspension flowing through a pipe is provided. A hinged collar is adapted to be secured around a section of pipe. A radiant energy source is mounted at a first position on the circumference of the hinged collar, and means is provided for diffusing the radiant energy from the soure and introducing the diffused energy into the section of pipe. A first radiant energy detector is mounted at a second position on the circumference of the hinged collar for sensing diffused energy in the pipe which is forward-scattered when a suspension is flowing therethrough. A second radiant energy detector is mounted at a third position on the circumference of the collar adjacent the first position, for sensing diffused energy in the pipe which is back-scattered when a suspension is flowing therethrough. Electrical connector means is mounted to the collar for connecting the radiant energy source and the first and second detectors to the apparatus for measuring solid particle percentage.

In a preferred embodiment, the hinged collar is adapted to be secured around a section of transparent pipe, and the collar comprises a material which serves to diffuse the energy emitted from the radiant energy source. In an alternate embodiment, the collar can be adapted to be secured around a section of translucent pipe which serves as the diffusing means.

The radiant energy source, in a preferred embodiment, comprises a plurality of emitters arranged in a circle around the second radiant energy detector. Electrical connections to the radiant energy source and detectors can be made through the use of one or more circuit boards mounted in the hinged collar. The circuit broads can be flexible so that they will curve to conform to the circumference of the collar. Channel means can be provided within the collar for accommodating electrical conductors which connect the source and detectors to the electrical connector means.

BRIEF DESCRIPTION OF THE DRAWINGS

FIG. 1 is a perspective view of a transducer mounting assembly in accordance with the present invention;

FIG. 2 is a plan view of the assembly of FIG. 1 mounted on a pipe;

FIG. 3 is a cross-sectional view taken substantially along the line 3—3 shown in FIG. 2;

FIG. 4 is a perspective view of the transducer mounting assembly of FIG 1 opened to show the interior and mechanical operation thereof.

DETAILED DESCRIPTION OF THE INVENTION

Figure 5:
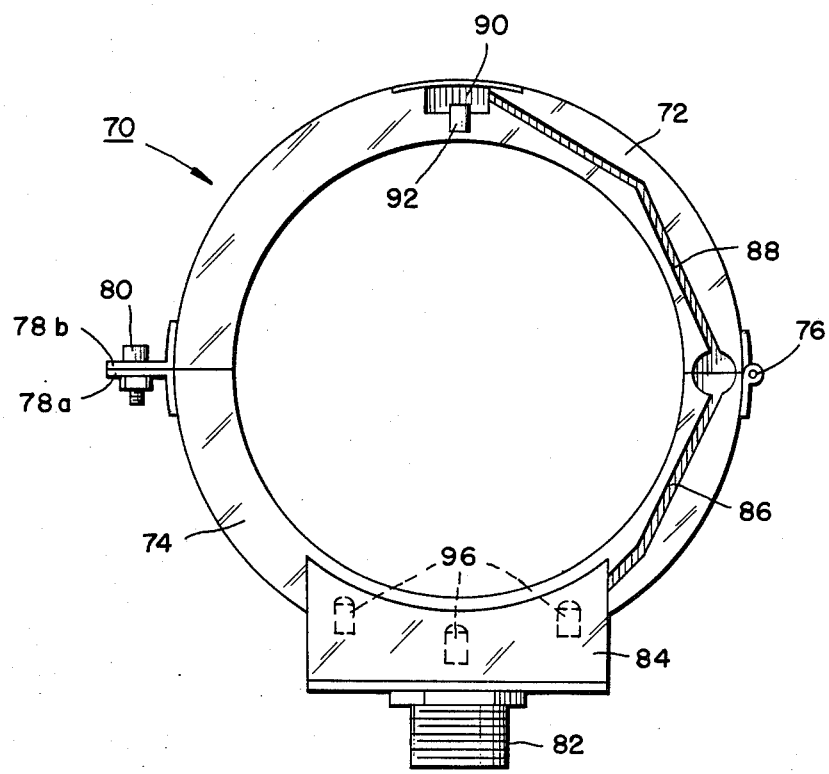
FIG. 5 is a top view of an alternate embodiment of a transducer mounting assembly in accordance with the present invention.

A transducer mounting assembly 10 is provided which can be readily attached to and detached from a section of pipe carrying a fluid without affecting or interrupting the fluid flow. In one embodiment, a hinged collar 11 is provided having a first semicircular collar member 14 and a second semiciruclar collar member 12. First semicircular collar member 14 comprises opposed flanges 15a and 15b supporting an outer wall 40 and an inner wall 46 therebetween. Second semicircular collar member 12 comprises opposed flanges 13a and 13b which support an outer wall 42 and an inner wall 44 therebetween. Flanges 15a, 15b, 13a, and 13b can be formed of any suitable rigid material, for example plastic or metal (e.g., aluminum). Outer walls 40 and 42 are typically plastic and can be secured to the flanges by screws, such as 41 and 43 shown in FIG. 1.

First semicircular collar member 14 and second semicircular collar member 12 are joined, at adjacent ends thereof, by a hinge 54. Hinge 54 may be any conventional type of hinge well known in the art. The other adjacent ends of first semicircular collar member 14 and second semicircular collar member 12 can be clamped together by clamp members 60a and 60b respectively. Clamp members 60a and 60b are detachably secured together by fasteners 56 and 58. Fasteners 56 and 58 can be any type of detachable fasteners known in the art, such as threaded nut and bolt arrangements. It is noted that the fasteners 56 and 58 depicted in the figures are meant to be merely illustrative, and not taken in any way to limit the scope of applicant's appended claims. For example, instead of using fasteners 56 and 58 as shown, a spring clip fastener or the like could be utilized. Other fasteners and clamping arrangements will be apparent to those skilled in the art.

First semicircular collar member 14 contains a flexible circuit board 18 which is sandwiched between outer wall 40 and inner wall 46. Circuit board 18 is curved to conform to the circumference of semicircular collar member 14 and is secured to flanges 15a and 15b by screws 20 and 22 respectively. Additional screws (not shown) are provided at the other end of flexible circuit board 18.

Flexible circuit board 18 contains electrical connection points to which a plurality of radiant energy sources 52a through 52h (see FIG. 4) and a radiant energy detector or sensor 50 can be mounted. Electrical conductors are provided in flexible circuit board 18 for connecting the radiant energy detector and sources to an electrical connector 16 extending from first semicircular collar member 14. For example, one radiant energy source can be mounted at electrical contact points 24 and 26 on flexible circuit board 18 and connected to connector 16 by conductors 23 and 25 respectively. Another radiant energy source can be connected to electrical connection points 28 and 30 for connection to connector 16 by conductors 27 and 29 respectively. Yet another radiant energy source can be connected via electrical connection points 32 and 34 conductors 31 and 33 to connector means 16. Any number of radiant energy sources and/or detectors can be mounted in this manner, depending upon the specific requirements of the measuring system with which the transducer mounting assembly 10 is being utilized.

In a preferred embodiment, for use in connection with an apparatus for determining the consistency of paper pulp stock, eight radiant energy sources 52a through 52h are arranged in a circle around a radiant energy detector 50, as shown in FIG. 4. An additional radiant energy detector 48 is mounted on a circuit board 62 which is sandwiched between outer wall 42 and inner wall 44 of second semicircular collar member 12. Again, although only one radiant energy detector 48 is shown mounted on circuit board 62, depending upon the requirements of the measuring system being used, additional detectors may be mounted on this circuit board. Like circuit board 18, circuit board 62 contains electrical connection points and conductors for connecting detector 48 to connector 16. A wire (not shown), passing from second semicircular collar member 12 to first semicircular collar member 14, or electrical contacts, can be used to provide the connection between circuit board 62 and connector 16.

The operation of the transducer mounting assembly of the present invention will now be explained with reference to FIGS. 2 and 3 of the drawings, and in connection with the measurement of the consistency of paper pulp stock. Transducer mounting assembly 10 is clamped around a transparent section 66 of a pipe 65. Pipe 65 has during pulp stock flowing therethrough during the normal operation of paper manufacturing machinery. Transparent section 66 of pipe 65 can be provided in a conventional manner, e.g. by joining the adjacent sections of a metal pipe 65 with a transparent glass or plastic pipe section. A cut-away view in FIG. 2 shows paper pulp stock 64 flowing through pipe 65.

Disfused radiant energy is introduced from radiant energy sources 52a–52h into pipe 65 containing paper pulp stock 64. The radiant energy emitted by sources 52a–52h can be diffused in any of several different ways. In the embodiment shown in FIGS. 1 through 4, inner wall 46 of semicircular collar member 14 is fabricated from a material which diffuses the radiant energy emitted from sources 52a–52h. Typically, inner wall 46 will be fabricated from plastic, which may be translucent if visible light is emitted from sources 52a–52h or can be visibly opaque if infra-red energy is emitted from the sources. The primary requirement of the material used for inner wall 46 in the embodiment shown is that it diffuses the energy emitted by the sources. Inner wall 44 of semicircular collar member 12 can be fabricated from the same energy diffusing material as inner wall 46. In an alternate embodiment, inner walls 46 and 44 can be transparent, and section 66 of pipe 65 can be fabricated from an energy diffusing material.

A suspension in pipe 65, e.g. paper pulp stock 64, will cause both forward-scattering and back-scattering of the diffused energy. In paper pulp stock, radiant energy is scattered by pulp fibers and transferred forward, backward and obliquely through the stock by the medium of unbound water which typically exists up to a consistency of approximately 15%. The mechanism by which the radiant energy is scattered by the pulp fibers is known as "multiple scattering", which is any scattering of a particle or photon in which the final displacement is the sum of many displacements, usually small. The number of reflections of the radiant energy from fiber surfaces in the stock, and hence the transfer path link, is in non-linear proportion to consistency. The radiant energy lost by reflection from the stock to the walls of pipe 65 is also in non-linear proportion to consistency; hence the energy collected by a detector diametrically opposite from an energy source is in non-linear inverse proportion to consistency. Similarly, the energy scattered back from pulp fibers in the srtock by way of the unbound water medium to a back-scattered radiation detector mounted adjacent the radiant source is in non-linear proportion to consistency. By combining the logarithmic equivalents of the detected forward-scattered and back-scattered energy, however, at a predetermined ratio, a linear measurement of consistency is achieved.

In the apparatus of the present invention, energy emitted by radiant energy sources 52a to 52h is diffused by walls 46 and 44 so that paper pulp stock 64 in pipe 65 is completely surrounded by radiant energy emitted by sources 52a to 52h. Those skilled in the art will appreciate that the magnitude of didffused energy will be greatest adjacent radiant energy sources 52a to 52h, and will decrease as the distance from sources 52a to 52h increases, as indicated by the arrows shown in FIG. 3 which emanate from transducer mounting assembly 10. Thus, the intensity of diffused radiant energy emitted into section 66 of pipe 65 from the transducer mounting assembly 10 will be greatest near radiation sensor 50, and will decrease as the energy travels, in a diffused manner, along inner walls 46 and 44 toward radiation sensor 48. An important feature of transducer mounting assembly 10, which results from the diffusion of radiant energy from sources 52a to 52h, is that the entire volume of section 66 of pipe 65 will be radiated by energy from sources 52a to 52h. In other words, radiation will be emitted throughout the entire inner circumference of transducer mounting assembly 10, but with the magnitude of radiation continuously decreasing as the distance from sources 52a to 52h along the circumference increases. Thus, the present apparatus enables the measurement of an entire sample.

When paper pulp stock 64 to be measured passes through pipe 65, the pulp stock will forward-scatter a portion of the energy from sources 52a to 52h and back-scatter a portion of the energy from the sources. As the percentages of solid particles in the suspension increases (increased consistency) the amount of back-scattered energy will increase and the amount of forward-scattered energy will decrease. As the percentage of solid particles in a suspension being measured goes down, the amount of forward-scattered energy will increase and the amount of back-scattered energy will decrease. Thus, at the theoretical outer limits, a suspension with a consistency of 100% will back-scatter all of the radiation and a suspension with a consistency of zero will not back-scatter any of the radiant energy from sources 52a–52h.

Back-scattered radiation sensor 50 and forward-scattered radiation sensor 48 can comprise photodetectors which provide an output current proportional to the amount of radiation impinging thereon. Such photodetectors are well known in the art. Radiation sensors 50 and 48 along with radiation sources 52a to 52h can be chosen to operate at infra-red wavelengths. In such a situation, radiation sources 52a to 52h will typically peak at a wavelength of about 0.96 microns, and radiation sensors 50 and 48 will detect wave lengths of about 0.8 microns and above. Those skilled in the art will appreciate that other wave lengths and types of radiant energy can alternatively be used in an apparatus of the present design. The selection of radiation type and wavelength will be determined in part by the sizes of solid particles which are present in a suspension to be measured.

FIG. 5 shows an alternate embodiment of a transducer mounting assembly 70 in accordance with the present invention. In this embodiment, a hinged collar comprising semicircular collar members 72 and 74 is adapted to be secured around a section of pipe. Radiant energy sources 96 are mounted at a first position on the circumference of collar member 74. Sources 96 can be arranged in a circle similar to the arrangement shown for sensors 52a to 52h in FIG. 4. A forward-scattered radiant energy detector 92 is mounted at a second position on the circumference of collar member 72 through the use of an appropriate mount 90 which can, for example, comprise a small circuit board.

A back-scattered radiant energy detector (not shown) is mounted at a third position on the circumference of collar member 74 adjacent radiant energy sources 96. In a preferred embodiment, the back-scattered radiant energy detector is mounted in the center of a circle defined by radiant energy sources 96 in a manner similar to that of back-scattered radiant energy detector 50 shown in FIG. 4. Radiant energy sources 96 and the back-scattered radiant energy detector are mounted in a mounting arrangement 84 which can comprise a circuit board for making electrical connections to sources 96 and the back-scattered radiant energy detector. A connector 82 is provided so that a measuring apparatus being used in conjunction with the transducer mounting assembly can be connected to sources 96 and the back-scattered and forward-scattered radiant energy detectors. A channel 86 is provided in collar member 74 along with a channel 88 in collar member 72 to provide for the passage of wires from forward-scattered radiant energy detector 92 to connector 82. Collar members 72 and 74 are hinged at one pair of adjacent ends thereof by a hinge 76. The other adjacent ends of collar members 72 and 74 are provided with a detachable clamping arrangement for securing transducer mounting assembly 70 around a section of pipe. For example, clamp member 78a and 78b can be provided along with a fastener 80 (e.g. nut and bolt) to provide the clamping arrangement. Other clamping arrangements will be apparent to those skilled in the art.

In the embodiment of FIG. 5, collar members 72 and 74 are formed from a material which diffuses the radiation from sources 96. Collar members 72 and 74 can, for example, be fabricated of translucent plastic. Alternatively, the mounting arrangement 84 can be fabricated from a diffusing material. It is noted that when infra-red radiation is emitted from sources 96, the diffusing material does not have to be translucent to visible light. In fact, in such an instance the diffusing material can be visably opaque; as long as it serves to diffuse the infra-red radiation.

Optical filters (not shown) can optionally be provided in a transducer mounting assembly in accordance with the present invention to exclude wavelengths shorter than a predetermined dimension, thereby excluding the detection of particular matter in the suspension being measured which is smaller than a specified size. For example, since pulp fiber diameters in paper pulp slurry range from 20 to 35 micrometers, optimum operation of the present apparatus can be achieved by using optical filters in front of the radiant energy detectors that exclude wavelengths shorter than 20 micrometers.

The present invention provides a transducer mounting assembly which, through its hinged arrangement, can be quickly mounted to or detached from a section of pipe through which a suspension to be measured is passing. Mounting of the assembly to the pipe does not require any disassembly of or intrusion into the pipe, except for providing a section of the pipe through which the emitted and detected radiated energy can pass. Although the invention has been described with reference to electrical radiation energy sources and detectors, it will be apparent to those skilled in the art that other arrangements, such as fiber optic means, can be alternatively provided for use with the transducer mounting assembly.

I claim:

1. transducer mounting assembly for use in conjunction with apparatus for measuring the percentage of solid particles in a suspension flowing through a pipe comprising:
   a hinged collar adapted to be secured around a section of pipe;
   a radiant energy source mounted at a first position on the circumference of said collar;
   means for diffusing radiant energy from said source and introducing said diffused energy into said section of pipe;
   a first radiant energy detector mounted at a second position on the circumference of said collar for sensing diffused energy in said pipe which is predominantly forward-scattered when a suspension is flowing therethrough;
   a second radiant energy detector mounted at a third position on the circumference of said collar opposite said first detector and adjacent said first position for sensing diffused energy in said pipe which is predominantly back-scattered when a suspension is flowing therethrough; and
   connector means mounted to said collar for connecting said radiant energy source and first and second detectors to a measuring apparatus.

2. The assembly of claim 1 wherein said collar comprises a material which diffuses the radiant energy emitter from said source.

3. The assembly of claim 2 wherein said collar is adapted to be secured around a section of transparent pipe.

4. The assembly of claim 1 wherein said collar is adapted to be secured around a section of translucent pipe which serves as said diffusing means.

5. The assembly of claim 1 wherein said radiant energy source emits infra-red energy and said first and second detectors detect infra-red energy.

6. The assembly of claim 1 wherein said radiant energy source comprises a plurality of emitters arranged in a circle around said second radiant energy detector.

7. The assembly of claim 6 wherein said second position on the circumference of said collar is directly opposite said third position.

8. The assembly of claim 6 further comprising a flexible circuit board mounted in said collar and curved to conform to the circumference thereof, said circuit board including electrical connection points to which said radiant energy source and said second radiant energy detector are mounted for electrical connection to said connector means.

9. The assembly of claim 8 further comprising a second circuit board mounted in said collar adjacent said second position and including electrical connection points to which said first radiant energy detector is mounted for electrical connection to said connector means.

10. The assembly of claim 1 wherein said second position on the circumference of said collar is directly opposite said third position.

11. The assembly of claim 1 wherein said hinged collar comprises first and second semicircular sections having a hinge joining one pair of adjacent ends thereof, said assembly further comprising means for clamping the other adjacent ends of said sections together.

12. The assembly of claim 11 further comprising channel means within said collar for accommodating electrical conductors which connect said source and detectors to said connector means.

13. A transducer mounting assembly for use in conjunction with apparatus for measuring the percentage of said particles in a suspension flowing through a pipe comprising:
   a first semicircular collar member;
   a radiant energy source mounted on said first collar member and adapted to radiate energy toward the interior of the circle defined by said first collar;
   a back-scattered radiant energy detector mounted on said first collar member and adapted to detect energy returning from the interior of the circle defined by said first collar member;
   a second semicircular collar member;

a forward-scattered radiant energy detector mounted on said second collar member and adapted to detect energy returning from the interior of the circle defined by said second collar member;

hinge means coupling one end of said first collar member to one end of said second collar member for providing an articulating assembly adapted to be removably mounted around a section of pipe; and means for detachably securing the other ends of said first and second collar members together when said articulating assembly is positioned around a section of pipe.

14. The assembly of claim 13 further comprising means for diffusing radiant energy emitted from said radiant energy source.

15. The assembly of claim 13 wherein said first collar member comprises a translucent material positioned in front of said radiant energy source for diffusing radiant energy emitted from said source.

16. The assembly of claim 13 wherein said radiant energy source comprises a plurality of radiant energy emitters arranged in a circle around said back-scattered radiant energy detector.

17. The assembly of claim 16 wherein said radiant energy source emits infra-red energy and said back-scattered and forward-scattered detectors sense infra-red energy.

18. The assembly of claim 13 wherein said radiant energy source emits infra-red energy and said back-scattered and forward-scattered detectors sense infra-red energy.

19. The assembly of claim 13 wherein said radiant energy source and said radiant energy detectors comprise fiber optic means adapted to be coupled to an apparatus for measuring the percentage of solid particles in a suspension flowing through a pipe.

* * * * *